United States Patent [19]

Konishi et al.

[11] Patent Number: 4,518,589

[45] Date of Patent: May 21, 1985

[54] BBM-2478 ANTIBIOTIC COMPLEX

[75] Inventors: Masataka Konishi, Kawasaki; Koko Sugawara, Wakō; Takeo Miyaki, Yokohama; Hiroshi Kawaguchi, Tokyo, all of Japan

[73] Assignee: Bristol-Myers Company, New York, N.Y.

[21] Appl. No.: 538,453

[22] Filed: Oct. 3, 1983

[51] Int. Cl.³ .................. A61K 31/71; C07H 15/24
[52] U.S. Cl. .................. 514/27; 536/16.8; 536/18.1; 536/17.2; 435/75
[58] Field of Search .......... 536/16.8, 18.1, 17.2; 424/180

[56] References Cited

PUBLICATIONS

Leach et al., *J. Am. Chem. Soc.* 75: 4011–4012, (1953).
Simonitsch et al., *Helv. Chim. Acta* 47: 1439:1484, (1964).

*Primary Examiner*—Johnnie R. Brown
*Assistant Examiner*—Elli Peselev
*Attorney, Agent, or Firm*—David M. Morse

[57] ABSTRACT

A novel antibiotic complex designated BBM-2478 is produced by fermentation of an actinomycete strain J907-21 (ATCC 39417). The complex may be separated chromatographically into two bioactive components designated BBM-2478A and BBM-2478B. The BBM-2478A component displays both antibacterial and antitumor activity while the BBM-2478B component has antibacterial activity.

8 Claims, 4 Drawing Figures

FIG. 1

INFRARED ABSORPTION SPECTRUM OF BBM-2478A

FIG. 3
PROTON NMR SPECTRUM OF BBM-2478A

FIG. 4

13C NMR SPECTRUM OF BBM-2478A

BBM-2478 ANTIBIOTIC COMPLEX

BACKGROUND OF THE INVENTION

1. Field of the Invention

This invention relates to a new antitumor antibiotic complex and to its production, recovery and separation into two bioactive components.

2. Description of the Prior Art

The two antibiotic compounds of the present invention are glycosides composed of an aglycone, chartarin, the aglycone of chartreusin, and either one or two sugar moieties. BBM-2478B has one sugar moiety of the formula attached to the aglycone while BBM-2478A, the other antibiotic of the present invention, has in addition the amino sugar of the formula The antibiotic chartreusin disclosed, for example, in *J. Am. Chem. Soc.* 75: 4011–4012 (1953) and *Helv. Chim. Acta* 47: 1459–1484 (1964) has the same aglycone portion as the present antibiotics but contains two different sugars, i.e. D-fucose and D-digitalose. Chartreusin has the structure and is produced by fermentation of *Streptomyces chartreusis*, Streptomyces Sp. No. 747 (*S. viridis*), Streptomyces Sp. 6A36 (*S. viridochromogenes*) and by two actinomycete strains designated Streptomyces Sp. X-3988 and S-465. Chartreusin is apparently the same as antibiotic 747 and antibiotic X-465A.

SUMMARY OF THE INVENTION

There is provided by the present invention a new antibiotic complex designated BBM-2478, said complex being produced by cultivating an actinomycete strain designated strain J907-21 (ATCC 39417), or variants or mutants thereof, in an aqueous nutrient medium containing assimilable sources of carbon and nitrogen under submerged aerobic conditions until a substantial amount of BBM-2478 complex is produced by said organism in said culture medium and, subsequently, recovering the BBM-2478 complex from the culture medium. The BBM-2478 complex contains two bioactive component antibiotics designated BBM-2478A and BBM-2478B which may be separated by conventional chromatographic procedures and isolated in substantially pure form.

BBM-2478A and B exhibit antibacterial activity against aerobic gram-positive bacteria and anaerobic bacteria. BBM-2478A also inhibits the growth of malignant tumors in experimental animal tumors.

DETAILED DESCRIPTION

This invention relates to novel glycoside antibiotics designated herein as BBM-2478A and BBM-2478B and to their preparation by fermentation of an actinomycete strain designated strain J907-21. The producing organism isolated from a soil sample collected in El Salvador, has been classified at the present time only as a non-Streptomyces actinomycete strain. A biologically pure culture of this organism has been prepared by conventional procedures and deposited in the American Type Culture Collection, Washington, D.C., under the accession number ATCC 39417.

Taxonomy of the Producing Culture

Strain J907-21 forms well-branched, non-fragmenting vegetative mycelia, but lacks the ability of bearing true aerial mycelia. It is asporogenic as examined to date. Since it contains meso-diaminopimelic acid in the cell wall and madurose in the whole cell hydrolyzate, strain J907-21 is placed in cell wall Type $III_B$. Strain J907-21 does not bear any morphologically important bodies such as spore chain and sporangium. Thus, at the present time, strain J907-21 can only be classified as a non-Streptomyces actinomycete strain.

Morphology

Strain J907-21 forms long well-branched vegetative mycelia (0.4 μm in width) which do not fragment into rod or coccoid cell. Rudimental short aerial mycelia are occasionally formed on some agar media, but a true aerial mycelium is not formed on all descriptive media. Spore-forming bodies and spores are not observed so far as examined.

Cultural Characteristics

As shown in Table 1, the strain grows moderately on natural organic media but poorly on most chemically defined media. Although strain J907-21 does not form a true aerial mycelium, rudimental short aerial mycelia are partially formed on ISP Nos. 2 and 4 media and Bennett's agar. The rudimental aerial mycelium is formed also in ISP No. 7 medium supplemented with cobalamine or vitamine complex. The reverse side color of vegetative mycelia is pale yellow to various shades of brown on most agar media. Deep reddish mycelial pigment is produced on ISP No. 2 medium and VDYA (V8 juice-dextrose-yeast extract agar). Melanoid pigment is no produced in ISP Nos. 1, 6 and 7 media. Colony on ISP No. 2 medium is extremely raised, rigid and folded.

Physiological Characteristics

Maximal growth is observed at 28° C. and 37° C. No growth is seen at 7° C. and 45° C. The growth ranges from 15° C. to 43° C. Melanin is not formed from L-3,4-dihydroxy-phenylalanine (L-DOPA). Strain J907-21 is tolerant to sodium chloride at 4% or less but not at 5%, and is sensitive to lysozyme. Strain J907-21 utilizes almost all pentoses and hexoses. The physiological characteristics and carbohydrate utilization are shown in Tables 2 and 3, respectively.

Cell-Wall Amino Acid and Whole Cell Sugar Components

The amino acid composition in cell wall was examined according to the methods described by Becker et al. in *Appl. Microbiol.* 13: 236–243 (1965) and by Yamaguchi in *J. Bacteriol,* 89: 444–453 (1965) and was also determined by the amino acid analyzer (Hitachi 0342U Model). The sugar component in the whole cell hydrolyzate was identified according to the procedures outlined by Lechevalier and Lechevalier in *Chemical Methods As Criteria For The Separation Of Nocardiae From Other Actinomycetes. Biology Of The Actinomycetes And Related Organisms* 11: 78–92 (1976). The cell wall of strain J907-21 contains meso-diaminopimelic acid and a small amount of glycine. The whole cell hydrolyzate shows the presence of glucose, mannose, madurose and ribose. The above-mentioned cell wall composition and whole cell sugar components indicate that strain J907-21 belongs to cell-wall type $III_B$.

Taxonomy

Strain J907-21 which is a mesophilic, gram-positive actinomycete, occasionally forms rudimental short aerial mycelia, but lacks the ability of forming a true aerial mycelium, spore-bearing body and spore. Strain J907-21 has a Type $III_B$ cell wall. Known actinomycetes which have Type $III_B$ cell wall include genera Actinomadura, Microbispora, Streptosporangium, Spirillospora, Planomonospora, Planobispora and Dermatophilus. The vegetative mycelium of genus Dermatophilus which is an obligate animal pathogen in nature, exhibits both transverse and longitudinal septations. Therefore, strain J907-21 is clearly differentiated from the genus Dermatophilus. Remaining six genera are characterized by bearing on the aerial mycelium a spore vesicle (sporangium) or arthrospore. While unlike the species of Streptomyces, many strains of these six genera are reported to be more or less fastidious in sporulation. Hence, strain J907-21 probably belongs to one of the six genera mentioned above. Among the six genera, the genus Actinomadura has been reported to be a soil inhabitant widely distributed in the world. Gordon in *J. Gen. Microbiol.* 109: 69–78 (1978) characterized physiologically 14 taxa of nocardiae inducing *Actinomadura madurae*. Based on Gordon's physiological examinations, strain J907-21 was compared with *A. madurae* (Table 4). Strain J907-21 was more closely related to *Actinomadura madurae* (similarity at 85.7%) than to the other taxa having cell wall types $III_C$ and IV (similarity: 54.8%~76.9%). However, the physiological relationships among the six genera having Type $III_B$ cell wall have not been established because they are distinctly different from each other in morphology. Thus, strain J907-21 can only be classified as an asporogenic non-Streptomyces.

TABLE 1

| Cultural Characteristics* of Strain No. J907-21 | |
|---|---|
| Tryptone-yeast extract broth (ISP No. 1) | G**: poor; floccose, pale yellow pellets |
| | D: none |
| Sucrose-nitrate agar (Czapek's agar) | G: poor |
| | R: yellowish white (92)*** to light olive brown (94) |
| | A: none |
| | D: none |
| Glucose-asparagine agar | G: poor |
| | R: yellowish white (92) to moderate olive brown (95) |
| | A: none |
| | D: none |
| Glycerol-asparagine agar (ISP No. 5) | G: poor |
| | R: light grayish yellowish brown (79) to dark grayish yellowish brown (81) |
| | A: none |
| | D: moderate yellowish brown (77) |
| Inorganic salts-starch agar (ISP No. 4) | G: poor |
| | R: grayish yellowish brown (80) |
| | A: no or very scant; if formed, rudimental, yellowish white (92) |
| | D: dark grayish yellowish brown (81) |
| Tyrosine agar (ISP No. 7) | G: moderate |
| | R: grayish yellow (90) to deep yellowish brown (75) |
| | A: none |
| | D: none |
| Nutrient agar | G: poor |
| | R: deep yellow (85) to dark olive brown (96) |
| | A: none |
| | D: none |
| Yeast extract-malt extract agar (ISP No. 2) | G: moderate |
| | R: dark grayish yellow (91) to dark olive brown (96) |
| | A: no or very scant; if formed, rudimental, light grayish yellowish brown (79) |
| | D: dark yellowish brown (78) |
| Oat meal agar (ISP No. 3) | G: moderate |
| | R: yellowish white (92) to grayish yellow (90) |
| | A: none |
| | D: none |
| Bennett's agar | G: moderate |
| | R: dark grayish yellow (91) to dark olive brown (96) |
| | A: no or very scant; if formed, rudimental, yellowish white (92) |
| | D: deep yellow (85) |
| Peptone-yeast extract-iron agar (ISP No. 6) | G: moderate |
| | R: light olive brown (94) to deep yellowish brown (75) |
| | A: none |
| | D: brilliant orange yellow (67) |
| VDYA agar (Papavizas, 1964) | G: abundant |
| | R: vivid deep red (14) to blackish red (21) |
| | A: none |
| | D: dark red (16) |
| Corn meal agar (Riker & Riker, 1936) | G: abundant |
| | R: deep yellowish brown (75) to dark yellowish brown (78) |
| | A: none |
| | D: strong brown (55) |
| C-2 agar (Nonomura, 1971) | G: poor |
| | R: light yellowish brown (76) to deep yellowish brown (75) |
| | A: no or very scant; if formed, rudimental, white (263) |

TABLE 1-continued

**Cultural Characteristics\* of Strain No. J907-21**

| | |
|---|---|
| Potato-carrot agar (Cross et al., 1963) | D: none<br>G: poor to moderate<br>R: grayish yellow (90) to dark yellowish brown (78)<br>A: none<br>D: dark yellowish pink (30) |
| Colony on ISP No. 2 medium: | good growth; extremely raised, hard and folded; 3~5 mm in diameter, reddish black (24) surface color, formation of no or rudimental aerial mycelium |

*observed after incubation at 28° C. for 3 weeks
**Abbreviation: G = growth; R = reverse color; A = aerial mycelium; D = diffusible pigment
***Color and number in parenthesis follow the color standard in "Kelly, K. L. & D. B. Judd: ISCC-NBS color-name charts illustrated with Centroid Colors. U.S. Dept. of Comm. Cir. 553, Washington, D.C., Nov., 1975".

TABLE 2

Physiological Characteristics of Strain No. J907-21

| Test | Response | Method or medium used |
|---|---|---|
| Range of temperature for growth | Maximal growth at 28° C. to 37° C. Growth range from 15° C. to 43° C. No growth at 7° C. and 45° C. | Bennett's agar |
| Gelatin liquefaction | Liquefied | 1% malt extract, 0.4% yeast extract, 0.4% glucose, 20% gelatin |
| Starch hydrolysis | Hydrolyzed | Starch agar plate |
| Reactions in skimmed milk | Not coagulated and completely peptonized | Difco skimmed milk |
| Formation of melanoid pigment | Negative | Tyrosine agar, peptone-yeast extract-iron agar, and tryptone-yeast extract broth |
| Tyrosinase reaction | Negative | Aria's method* |
| Nitrate reduction | Negative | 0.5% yeast extract, 1% glucose, 0.5% KNO$_3$, 0.1% CaCO$_3$ |
| pH tolerance | Growth in pH 5.0~11.0. No growth at pH 4.5. | Yeast extract-malt extract agar |
| NaCl tolerance | Growth at 4% NaCl or less. No growth at 5% NaCl. | Basal medium: 1% yeast extract, 2% soluble starch, 1.5% agar |
| Lysozyme tolerance | Sensitive. No growth at 0.001% lysozyme. | Trypticase soy broth plus 1.5% agar |

Arai, T. and Y. Mikami: Chromogenicity of Streptomyces. Appl. Microbiol. 23: 402–406, 1972.

TABLE 3

Carbohydrate Utilization of Strain No. J907-21

| | |
|---|---|
| Glycerol | + |
| D(−)-Arabinose | + |
| L(+)-Arabinose | + |
| D-Xylose | + |
| D-Ribose | + |
| L-Rhamnose | + |
| D-Glucose | + |
| D-Galactose | + |
| D-Fructose | + |
| D-Mannose | + |
| L(−)-Sorbose | − |
| Sucrose | − |
| Lactose | − |
| Cellobiose | + |
| Melibiose | − |
| Trehalose | + |
| Raffinose | − |
| D(+)-Melezitose | − |
| Soluble starch | + |
| Cellulose | − |
| Dulcitol | − |
| Inositol | + |
| D-Mannitol | + |
| D-Sorbitol | − |
| Salicin | + |

Observed after incubation at 37° C. for 3 weeks.
Basal medium: Pridham-Gottlieb's inorganic medium
Abbreviation: +: positive utilization. −: negative utilization.

TABLE 4

**Comparison of Diagnostic Physiological Properties Between Strain J907-21 and *Actinomadura madurae***

| | Strain J907-21 | *Actinomadura\* madurae* (47)** |
|---|---|---|
| Decomposition of: | | |
| Adenine | + | − |
| Casein | + | + |
| Hypoxanthine | + | + |
| Tyrosine | + | + |
| Urea | − | − |
| Xanthine | − | − |
| Resistance to: | | |
| Lysozyme | − | − |
| Rifampin | + | v |
| Hydrolysis of: | | |
| Aesculin | + | + |
| Hippurate | + | − |
| Starch | + | + |
| Acid from: | | |
| Arabinose | + | + |
| Cellobiose | + | + |
| Glucose | + | + |
| Glycerol | + | + |
| Inositol | + | v |
| Lactose | − | v |
| Mannitol | + | + |
| Mannose | + | + |
| Melezitose | − | − |
| Melibiose | − | − |
| Raffinose | − | − |
| Rhamnose | + | + |
| Sorbitol | − | − |
| Trehalose | + | + |
| Xylose | + | + |
| Utilization of: | | |
| Benzoate | − | − |
| Citrate | − | v |
| Mucate | − | − |
| Succinate | + | v |
| Tartrate | − | − |
| Nitrate from nitrate | − | + |
| Survival at 50° C., 8 h | − | + |

+: positive, −: negative, v: 15 to 84% of the strains positive
*Data of Gordon et al.
**No. of strains examined As in the case of other organisms, the characteristics of strain J907-21 are subject to variation. For example, artificial variants and mutants of the J907-21 strain may be obtained by treatment with various known mutagens such as ultraviolet rays, X-rays, high frequency waves, radioactive rays and chemicals. All natural and artificial variants and mutants (hereinafter referred to as mutants) of strain J907-21 which produce the BBM-2478 antibiotics are intended to be included within the scope of the present invention.

Antibiotic Production

The BBM-2478 antibiotics of the present invention are produced by cultivating strain J907-21 (ATCC 39417) or a BBM-2478-producing mutant thereof under submerged aerobic conditions in an aqueous nutrient medium. The producing organism is grown in a nutrient medium containing an assimilable carbon source, for example an assimilable carbohydrate. Examples of suitable carbon sources include glycerol, arabinose, xylose, glucose, fructose, mannose, soluble starch, mannitol and cellobiose. The nutrient medium should also contain an assimilable nitrogen source such as fish meal, soybean meal, corn steep liquor, peptones, meat extract, peanut flour, yeast extract or ammonium salts. Inorganic salts such as sodium chloride, potassium chloride, magnesium sulfate, calcium carbonate, phosphates, etc. are added if necessary. Trace elements such as copper, manganese, iron, zinc, etc. are added to the medium if desired, or they may be supplied as impurities of other constituents of the media. The incubation temperature may be any temperature at which the producing strain is able to grow, e.g. 15° to 43° C., but if it is preferable to conduct the fermentation at 25°-35° C., especially 27°-32° C. A neutral or near neutral pH is preferably employed in the medium and production of antibiotic is generally carried out for a period of about 6-10 days. Ordinarily, optimum production is achieved in about 6-7 days. For preparation of relatively small amounts, shake flasks and surface culture can be employed, but for the preparation of larger amounts, submerged aerobic culture in sterile tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. Aeration in tanks and bottles may be provided by forcing sterile air through or onto the surface of the fermenting medium. Further agitation may be provided by a mechanical impeller. Antifoaming agents such as lard oil may also be added if needed.

Production of BBM-2478 in the fermentation medium can readily be followed during the course of fermentation by the paper disc-agar diffusion assay using *Micrococcus luteus* PCI 1001 as the test organism.

Isolation of the BBM-2478 Antibiotics

After optimum broth potency has been obtained, the mycelium and undissolved residues are separated from the fermentation broth by conventional means such as filtration or centrifugation. Antibiotic in the mycelial cake may be recovered by extracting the mycelial cake with methanol, filtering off insoluble materials and concentrating the methanol extract to an aqueous solution. Activity in the broth supernatant may be recovered by extraction with n-butanol and concentration of the butanol extract to an aqueous solution. The aqueous methanol and butanol extracts containing the BBM-2478A and B antibiotics may then be subjected to conventional chromatographic purification procedures so as to provide purified BBM-2478A and B. A preferred purification procedure is described in Example 2 which follows.

Physico-chemical Properties of BBM-2478 Antibiotics

Figure 1:
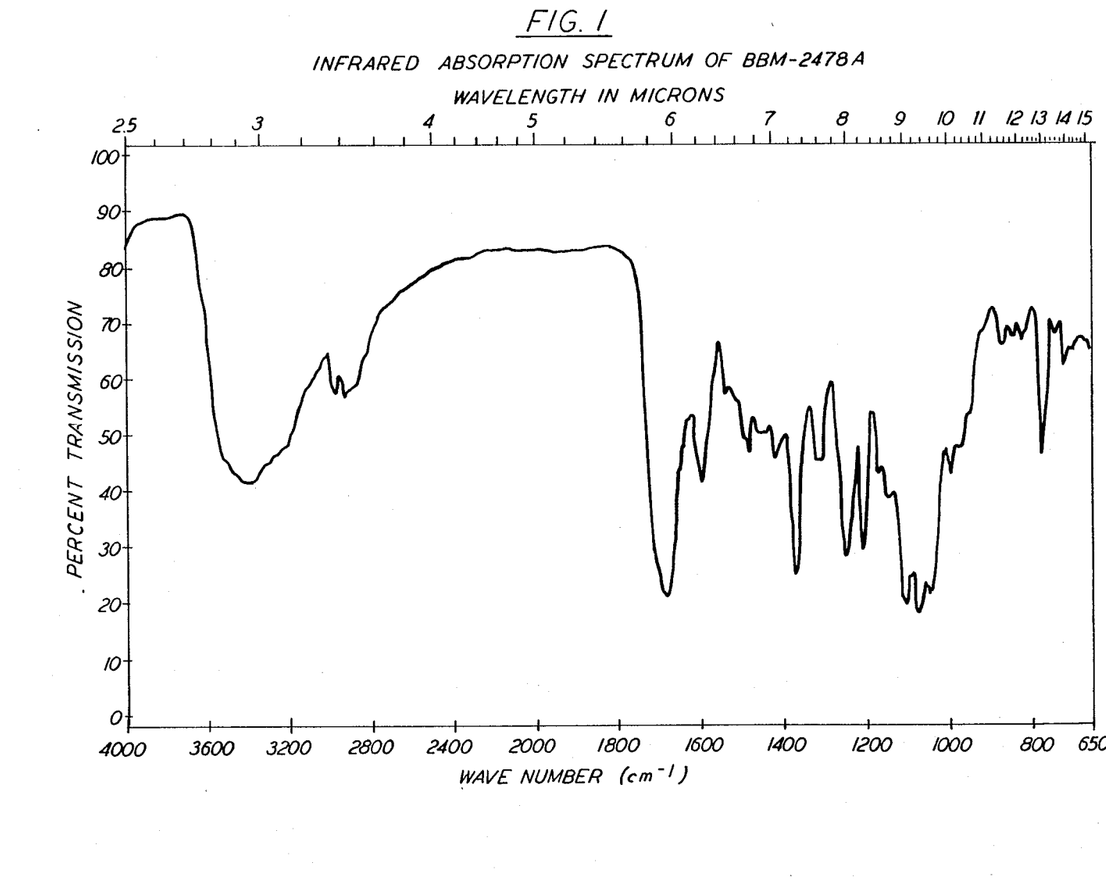
FIG. 1 shows the infrared absorption spectrum of BBM-2478A.
Figure 2:
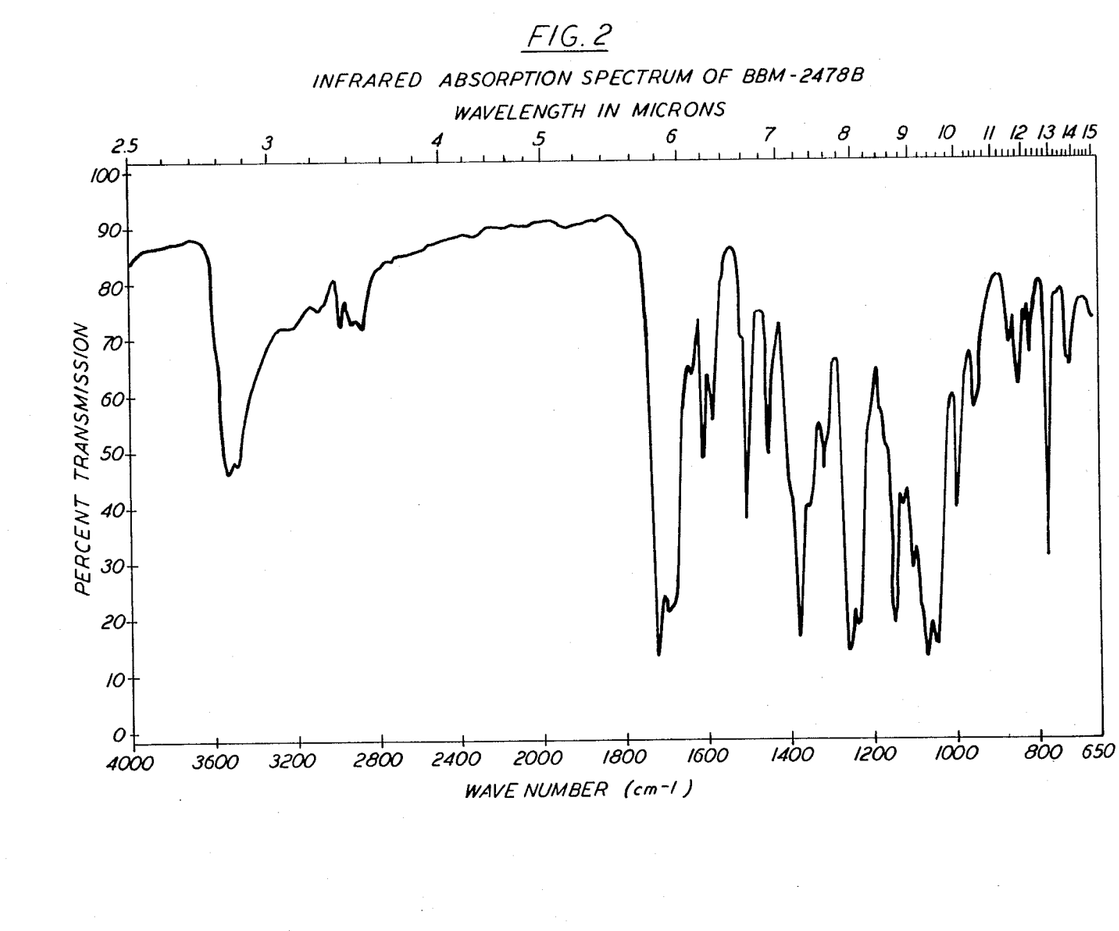
FIG. 2 shows the infrared absorption spectrum of BBM-2478B.
Figure 3:
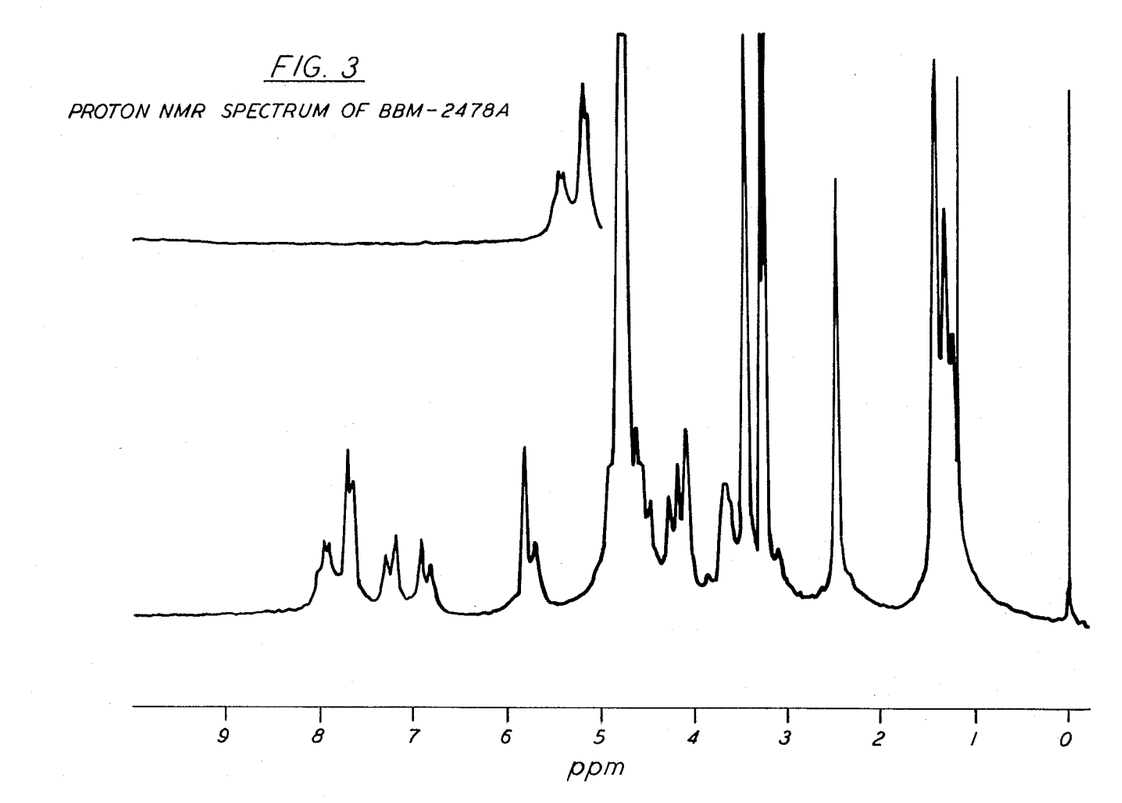
FIG. 3 shows the proton magnetic resonance spectrum (80 MHz) of BBM-2478A in $CD_3OD$.
Figure 4:
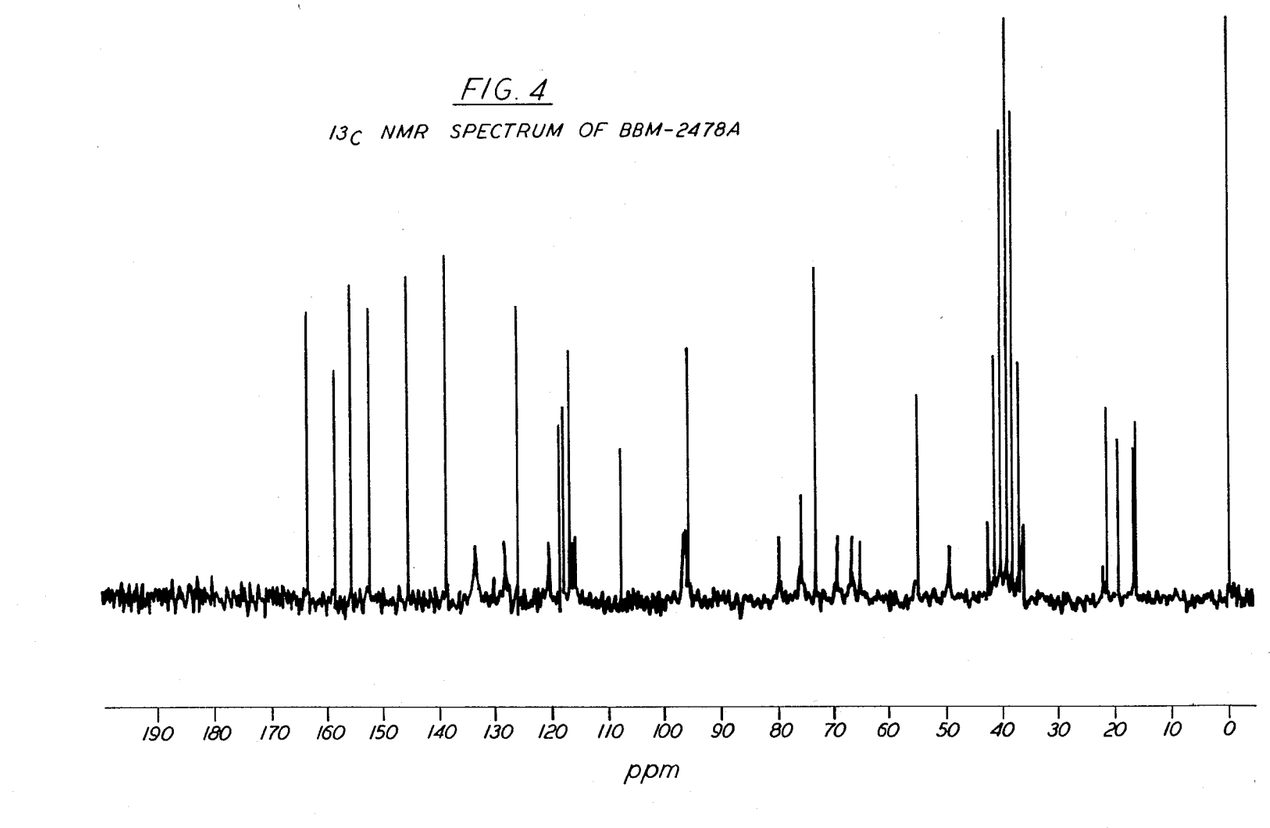
FIG. 4 shows the $^{13}C$ nuclear magnetic resonance spectrum (20 MHz) of BBM-2478A in $d_6$-DMSO.

BBM-2478 A and B were obtained as yellowish-orange crystalline solids. Both components of BBM-2478 are distinguishable from chartreusin by thin layer chromatography (TLC) as shown in Table 5. BBM-2478A is readily soluble in dimethyl sulfoxide, dimethylformamide, dioxane and acidic water, slightly soluble in methanol, ethanol and chloroform and insoluble in other organic solvents. Solubility of BBM-2478B is similar to that of BBM-2478A except that BBM-2478B is insoluble in acidic water. BBM-2478 A and B give positive responses with ferric chloride and anthrone reagents. BBM-2478A shows positive reaction to ninhydrin, while BBM-2478B is negative in the same test. Tollen's and Sakaguchi reactions are negative with both components. The physico-chemical properties of BBM-2478A and B are summarized in Table 6. The UV spectra of the two components are similar, showing maxima at 236, 266, 398 and 422 nm in neutral and acidic solutions and at 240, 268 and 435 nm in alkaline solution. These spectra are closely related to that of chartreusin. The IR spectra of BBM-2478 A and B are illustrated in FIGS. 1 and 2, respectively. The proton (PMR) and $^{13}$C-NMR (CMR) spectra of BBM-2478A are shown in FIGS. 3 and 4.

TABLE 5

| TLC of BBM-2478 A and B and Chartreusin | | |
|---|---|---|
| | $SiO_2$ $CHCl_3$—MeOH (7:3) | $SiO_2$ EtOAc—MeOH (1:1) |
| BBM-2478A | Rf 0.37 | 0.16 |
| BBM-2478B | 0.78 | 0.57 |
| Chartreusin | 0.65 | 0.48 |

TABLE 6

| Physico-chemical Properties of BBM-2478 A and B | | |
|---|---|---|
| | BBM-2478 A | BBM-2478 B |
| Nature | Yellow amorphous powder | Yellow amorphous powder |
| M.p. | 225~226° C. | 271~272° C. (dec.) |
| $[\alpha]_D^{26}$ (c 0.5, pyridine) | +124° | −8° |
| UV $\lambda_{max}^{MeOH}$ nm ($E_{1\ cm}^{1\%}$) | 236 (590) | 236 (740) |
| | 266 (550) | 266 (700) |
| | 333 (100) | 333 (118) |
| | 378 (132) | 378 (169) |
| | 398 (205) | 398 (255) |
| | 422 (225) | 422 (290) |
| Analysis Found: | C 59.28 | C 63.07 |
| | H 5.40 | H 4.51 |
| | N 2.06 | |

TABLE 6-continued
Physico-chemical Properties of BBM-2478 A and B

|  | BBM-2478 A | BBM-2478 B |
|---|---|---|
| Calc'd for: | $C_{33}H_{35}NO_{13}\cdot H_2O$ | $C_{26}H_{22}O_{10}$ |
|  | C 59.01 | C 63.16 |
|  | H 5.55 | H 4.48 |
|  | N 2.09 |  |

Structural Studies on BBM-2478 Antibiotics

The CMR spectrum of BBM-2478A demonstrated the presence of 33 carbons including four C—$\underline{C}H_3$, one —O$\underline{C}H_3$, nine >$\underline{C}H$—, one >$\underline{C}$<, five —$\underline{C}H=$ and 13 >$\underline{C}=$ groups. These CMR spectral data combined with the microanalytical data on BBM-2478A deduced a molecular formula of $C_{33}H_{35}NO_{13}$ for the antibiotic. BBM-2478A was hydrolyzed with 0.4N methanolic hydrogen chloride under reflux for one hour. Yellow crystals which precipitated were collected by filtration and the filtrate concentrated in vacuo to afford a syrup containing ninhydrin-positive sugar fragments. The crystalline material was identified as chartarin, the aglycone of chartreusin, by comparative spectral analysis with an authentic sample.

Chartarin

The sugar fragment contained in the aqueous concentrate was the anomeric mixture of a disaccharide (compound I), which was separated by Amberlite CG-50 ($NH_4^+$ form) chromatography to give α and β methyl glycosides (Ia and Ib) in nearly equal amount. Molecular formulae of compounds Ia and Ib were both established as $C_{15}H_{29}NO_8$ based on the mass ($M^+ + 1$:m/z 352) and CMR spectra. Physico-chemical properties of Ia and Ib are summarized in Table 7. Compounds Ia and Ib resisted further acid hydrolysis and caused extensive decomposition of the resulting sugar fragments under acidic condition severe enough to cleave the glycoside linkage. A mixture of compound Ia and Ib (370 mg) was acetylated in methanol to afford a mono-N-acetyl derivative (460 mg, $M^+ + 1$:m/z 394) which was hydrolyzed in 4.5N methanolic hydrogen chloride. The product was chromatographed on a column of silica gel with the lower phase of $CHCl_3$—MeOH—c.$NH_4OH$ (6:1:1) to give α- and β-anomers of an N-acetyl amino sugar (compound N-Ac-IIa, 140 mg and N-Ac-IIb, 22 mg) and of a neutral sugar (compound IIIa, 85 mg and IIIb, 79 mg). When treated with saturated $Ba(OH)_2$ solution, N-Ac-IIa was quantitatively converted to the free amino form (compound IIa). The physico-chemical data of IIa, IIIa and IIIb are shown in Table 8. IIa was determined to be methyl 2-amino-2,6-dideoxy-3-O-methyl-α-D-galactopyranoside from the analysis of its NMR spectrum. As shown in Table 8, the NMR spectrum of IIa included 5 ring protons along with two O$\underline{C}H_3$ and one C—$\underline{C}H_3$ signals. First order analysis of the ring protons indicated coupling constants $J_{1-2}=3.8$, $J_{2-3}=10.5$, $J_{3-4}=3.0$, $J_{4-5}<1.0$ and $J_{5-6}=6.4$ Hz, which are compatible with the assigned structure. Furthermore, physico-chemical data of N,O-diacetyl IIa m.p. 163°~164° C. and $[\alpha]_D^{23}$: +154° (c 0.3, $CHCl_3$)) are similar to those reported for methyl 2-acetamido-4-O-acetyl-2,6-dideoxy-3-O-methyl-α-D-galactopyranoside by M. B. Perry in *Can. J. Chem.* 52: 3251–3255 (1974).

IIa: $R_1$ = $OCH_3$, $R_2$ = H
IIb: = H, = $OCH_3$

The PMR spectrum of IIIa indicated coupling constants of $J_{1-2}=4.5$, $J_{4-5}<1.0$ and $J_{5-6}=6.7$ Hz, while that of IIIb $J_{1-2}=7.8$, $J_{4-5}<1.0$ and $J_{5-6}=6.5$ Hz. The absence of a ring proton on $C_3$ was evident in both spectra. The spectral analysis indicated that IIIa and IIIb were, respectively, the α- and β-methyl glycoside of 6-deoxy-3-C-methylgulopyranoside (methyl virenoside) or 6-deoxy-3-C-methylgalactopyranoside. The authentic sample of methyl β-D-virenoside was shown to be different from IIIb by TLC and NMR spectrum: the $H_1$ and $H_5$ signals of methyl virenoside were observed considerably lower field than those of IIIb, indicating that $C_3$—OH of methyl virenoside was in axial orientation whereas that of IIIb was equatorial in orientation. D-Configuration was assigned for III based on optical rotational values of IIIa and IIIb and $\Delta[M]^{CuAm}$ observed for IIIa ($-1309°$). Thus, IIIa and IIIb were determined to be methyl 6-deoxy-3-C-methyl-α- and β-D-galactopyranoside, respectively.

IIIa: $R_1$ = $OCH_3$, $R_2$ = H
IIIb: = H, = $OCH_3$

The linkage of the two sugars was established by mass spectra of Ia and Ib and their acetates, which exhibited fragment ions assignable to a II→III sequence of the disaccharide. The 200 MHz PMR spectrum and decoupling experiment carried out for N,O-triacetyl-Ia revealed that sugar II bonded to $C_2$—OH of III by α-glycosidic linkage and therefore the structures of Ia and Ib were determined as shown below:

The UV spectra of BBM-2478A measured at various pH are very similar to those of chartreusin. This suggested that the disaccharide moiety of BBM-2478A is linked to chartarin at the same hydroxyl group as in chartreusin. The IR spectra of BBM-2478A and chartreusin in chloroform showed the same pattern of carbonyl absorption, supporting the above assignment. In the NMR spectrum of N-acetyl-BBM-2478A, the anomeric proton of III gave rise to a doublet with a spacing of J=8.0 Hz, which allowed the present inventors to assign a β-pyranoside conformation of III for the antibiotic.

The molecular formula of $C_{26}H_{22}O_{10}$ was assigned to BBM-2478B based on microanalysis. On mild acid methanolysis, BBM-2478B afforded chartarin and neutral sugars (IIIa and IIIb) identical with those obtained from BBM-2478A. Therefore, BBM-2478B is apparently the analog of BBM-2478A having no amino sugar moiety (II). Thus, the structures of BBM-2478A and B were established as shown below:

TABLE 7
Physico-chemical Properties of Compounds Ia and Ib

|  | Compound Ia | Compound Ib |
|---|---|---|
| Nature | White powder | White powder |
| M.p. | 79~82° C. | 80~83° C. |
| $[\alpha]_D$ (c 1.0, $H_2O$) | +211° | +116° |
| TLC n-BuOH—AcOH—$H_2O$ (63:10:27) | Rf 0.19 | 0.15 |
| Molecular formula | $C_{15}H_{29}NO_8$ | $C_{15}H_{29}NO_8$ |
| Mass spectrum (m/z) | 352 ($M^+ +1$) | 352 ($M^+ +1$) |
|  | 319 | 319 |
|  | 235 | 235 |
|  | 160 | 160 |
| PMR (60 MHz in $D_2O$) δ in ppm | 1.25 (3H,d) | 1.23 (3H,d) |
|  | 1.28 (3H,d) | 1.26 (3H,d) |
|  | 1.37 (3H,s) | 1.29 (3H,s) |
|  | 3.03 (1H,d-d) | 3.07 (1H,d-d) |
|  | 3.41 (3H,s) | 3.44 (3H,s) |
|  | 3.46 (3H,s) | 3.54 (3H,s) |
|  | 3.6~4.5 (6H,m) | 3.4~4.4 (6H,m) |
|  | 3.90 (1H,d,J = 4.3 Hz) | 4.50 (1H,d,J = 8.0 Hz) |
|  | 4.98 (1H,d,J = 3.5 Hz) | 5.09 (1H,d,J = 3.5 Hz) |

TABLE 8
Physico-chemical Properties of Compounds IIa, IIIa and IIIb

|  | IIa | IIIa | IIIb |
|---|---|---|---|
| Nature | Pale yellow syrup | Pale yellow syrup | Pale yellow syrup |
| $[\alpha]_D$ | +106° (c 0.2,MeOH) | +152° (c 0.5,$CHCl_3$) | −33° (c 0.5,$CHCl_3$) |
| TLC:Rf |  |  |  |
| $CHCl_3$—MeOH—$NH_4OH$ (2:1:1) lower phase | 0.67 | 0.35 | 0.32 |
| n-BuOH—AcOH—$H_2O$ (63:10:27) | 0.20 | 0.47 | 0.40 |
| Molecular formula | $C_8H_{17}NO_4$ | $C_8H_{16}O_5$ | $C_8H_{16}O_5$ |
| PMR, 60 MHz in $D_2O$ δ in ppm | 1.26 (d,3H,6.4)* | 1.27 (d,3H,6.7) | 1.27 (s,3H) |
|  | 2.97 (d-d,1H,3.8 & 10.5) | 1.34 (s,3H) | 1.28 (d,3H,6.5) |
|  | 3.41 (s,3H) | 3.38 (s,3H) | 3.45 (br-s,1H) |
|  | 3.43 (s,3H) | 3.48 (br-s,1H) | 3.52 (d,1H,7.8) |
|  | 3.45 (d-d,1H,3.0 & 10.5) | 3.83 (d,1H,4.5) | 3.60 (s,3H) |
|  | 4.00 (q,1H,6.4) | 4.18 (q,1H,6.7) | 4.00 (q,1H,6.5) |

TABLE 8-continued

| Physico-chemical Properties of Compounds IIa, IIIa and IIIb | | |
|---|---|---|
| IIa | IIIa | IIIb |
| 4.02 (br-d,1H,3.0) | 4.75 (d,1H,4.5) | 4.39 (d,1H,7.8) |
| 4.72 (d,1H,3.8) | | |

*(multiplicity, proton, J in Hz)

Biological Properties

The minimum inhibitory concentration (MIC) of BBM-2478 was determined comparatively with chartreusin against various gram-positive and gram-negative bacteria and fungi, as well as some anaerobic organisms, by the serial two-fold agar dilution method. Nutrient agar medium was used for gram-positive and gram-negative bacteria, GAM agar medium for anaerobes and Sabouraud agar medium for fungi. As shown in Table 9, BBM-2478 A, B and chartreusin showed similar antibacterial spectra against gram-positive bacteria and anaerobes, while they were inactive against gram-negative bacteria and fungi. The anti-staphylococcal activity of BBM-2478A was two to four times higher than that of BBM-2478B or chartreusin.

The antitumor activity of BBM-2478A was determined in mice comparatively with chartreusin against lymphocytic leukemia P388, lymphoid leukemia L1210 and melanotic melanoma B16. The tumors were implanted intraperitoneally into BDF$_1$ mice at inoculum sizes of $10^6$, $10^5$ and $10^6$ cells per mouse, respectively. Test compounds were dissolved in 0.9% saline containing 10% dimethyl sulfoxide and graded doses of the antibiotic were administered intraperitoneally 24 hours after tumor implantation. The treatments were given once daily for 9 days (qd 1→9). The results are shown in Tables 10, 11 and 12. BBM-2478A was approximately 10 to 30 times more active than chartreusin in terms of minimum effective dose and achieved T/C values superior to those of chartreusin against all tumors tested. BBM-2478B was found to be devoid of antitumor activity. The acute toxicity of BBM-2478A was determined in mice (ddY strain) by single intraperitoneal administration, the LD$_{50}$ being 38 mg/kg.

TABLE 9

Antibacterial Activity of BBM-2478 A and B

| Test organism | MIC (mcg/ml) | | |
|---|---|---|---|
| | BBM-2478A | BBM-2478B | Chartreusin |
| *Staphylococcus aureus* 209P | 1.6 | 3.1 | 3.1 |
| *Staphylococcus aureus* Smith | 0.8 | 6.3 | 6.3 |
| *Bacillus subtilis* PCI 219 | 0.8 | 0.8 | 0.4 |
| *Micrococcus luteus* PCI 1001 | 0.8 | 3.1 | 0.8 |
| *Micrococcus flavus* D12 | 0.8 | 1.6 | 0.4 |
| *Escherichia coli* NIHJ | 100 | >100 | >100 |
| *Klebsiella pneumoniae* D11 | 100 | >100 | >100 |
| *Pseudomonas aeruginosa* D15 | 100 | >100 | >100 |
| *Candida albicans* IAM 4888 | >100 | >100 | >100 |
| *Cryptococcus neoformans* D49 | >100 | >100 | >100 |
| *Aspergillus fumigatus* IAM 2530 | >100 | >100 | >100 |
| *Trichophyton mentagrophytes* D155 | >100 | >100 | >100 |
| *Bacteroides fragilis* | 12.5 | | 6.3 |
| *Clostridium difficile* | 12.5 | | 25 |
| *Clostridium perfringens* | 6.3 | | 1.6 |
| *Propionibacterium acnes* | 6.3 | | 3.1 |

TABLE 10

Effect of BBM-2478 on P388 Leukemia

| | Dose, ip (mg/kg/day*) | MST (days) | T/C (%) | Average wt. change on day 5 (g) | Survivors on | |
|---|---|---|---|---|---|---|
| | | | | | day 5 | day 45 |
| BBM-2478A | 3 | 20.0 | 222 ** | −1.0 | 5/5 | 0/5 |
| | 1 | 21.5 | 239 | +0.8 | 6/6 | 0/6 |
| | 0.3 | 17.0 | 189 | +1.8 | 6/6 | 0/6 |
| | 0.1 | 14.5 | 161 | +1.2 | 6/6 | 0/6 |
| | 0.03 | 10.0 | 111 | +2.3 | 6/6 | 0/6 |
| | 0.01 | 10.0 | 111 | +2.0 | 6/6 | 0/6 |
| Chartreusin | 10 | 19.5 | 217 | +1.3 | 6/6 | 0/6 |
| | 3 | 15.0 | 167 | +1.5 | 6/6 | 0/6 |
| | 1 | 14.0 | 156 | +1.3 | 6/6 | 0/6 |
| | 0.3 | 10.5 | 117 | +2.0 | 6/6 | 0/6 |
| | 0.1 | 9.0 | 100 | +2.8 | 6/6 | 0/6 |
| Vehicle | — | 9.0 | — | +2.4 | 12/12 | 0/12 |

*qd 1 → 9
**Circle indicates significant antitumor effect

TABLE 11

Effect of BBM-2478 on L1210 Leukemia

| | Dose, ip (mg/kg/day*) | MST (days) | T/C (%) | Average wt. change on day 5 (g) | Survivors on day 5 | Survivors on day 45 |
|---|---|---|---|---|---|---|
| BBM-2478A | 3 | 12.0 | 150 ** | −0.1 | 6/6 | 0/6 |
| | 1 | 11.0 | 138 | +0.8 | 6/6 | 0/6 |
| | 0.3 | 10.5 | 131 | +1.3 | 6/6 | 0/6 |
| | 0.1 | 8.0 | 100 | +2.6 | 6/6 | 0/6 |
| | 0.03 | 8.0 | 100 | +2.9 | 6/6 | 0/6 |
| | 0.01 | 8.0 | 100 | +3.2 | 6/6 | 0/6 |
| Chartreusin | 10 | 11.5 | 144 | +1.3 | 6/6 | 0/6 |
| | 3 | 9.0 | 113 | +1.4 | 6/6 | 0/6 |
| | 1 | 9.0 | 113 | +1.9 | 6/6 | 0/6 |
| | 0.3 | 8.0 | 100 | +3.2 | 6/6 | 0/6 |
| | 0.1 | 8.0 | 100 | +3.1 | 6/6 | 0/6 |
| Vehicle | — | 8.0 | — | +2.8 | 12/12 | 0/12 |

*qd 1 → 9
**Circle indicates significant antitumor effect

TABLE 12

Effect of BBM-2478 on B16 Melanoma

| | Dose, ip (mg/kg/day*) | MST (days) | T/C (%) | Average wt. change on day 5 (g) | Survivors on day 5 | Survivors on day 45 |
|---|---|---|---|---|---|---|
| BBM-2478A | 3 | 41.5 | 296 ** | +1.5 | 6/6 | 0/6 |
| | 1 | 34.5 | 246 | +2.2 | 6/6 | 0/6 |
| | 0.3 | 25.5 | 182 | +2.5 | 6/6 | 0/6 |
| | 0.1 | 18.5 | 132 | +2.5 | 6/6 | 0/6 |
| | 0.03 | 16.0 | 114 | +2.0 | 6/6 | 0/6 |
| Chartreusin | 10 | 25.0 | 179 | +1.7 | 6/6 | 0/6 |
| | 3 | 20.5 | 146 | +2.3 | 6/6 | 0/6 |
| | 1 | 16.0 | 114 | +2.3 | 6/6 | 1/6 |
| | 0.3 | 14.0 | 100 | +1.8 | 6/6 | 0/6 |
| Vehicle | — | 14.0 | — | +2.3 | 10/10 | 0/10 |

*qd → 9
**Circle indicates significant antitumor effect

As shown above, BBM-2478A and B possess potent antibacterial activity against aerobic gram-positive bacteria and anaerobic bacteria and are thus useful in the therapeutic treatment of mammals and other animals for infectious diseases caused by such bacteria. Additionally these compounds may be utilized for other conventional applications of antibacterial agents such as disinfecting medical and dental equipment.

The significant antitumor activity shown by BBM-2478A against experimental mouse tumor systems indicates that BBM-2478A is also therapeutically useful in inhibiting the growth of experimental animal mammalian tumors.

The present invention, therefore, provides a method for therapeutically treating an animal host affected by a bacterial infection which comprises administering to said host an effective antibacterial dose of BBM-2478A or BBM-2478B, or a pharmaceutical composition thereof. Additionally, the present invention provides a method for therapeutically treating an experimental animal a mammalian host affected by a malignant tumor which comprises administering to said host a tumor-inhibiting dose of BBM-2478A, or a pharmaceutical composition thereof.

In another aspect the present invention provides a pharmaceutical composition which comprises an effective antibacterial amount of BBM-2478A or BBM-2478B in combination with an inert pharmaceutically acceptable carrier or diluent. Additionally, the present invention provides a pharmaceutical composition for treatment of experimental animal malignant tumors which comprises an effective tumor-inhibiting amount of BBM-2478A in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the BBM-2478 antibiotics used will vary according to the particular component, the particular composition formulated, the mode of application and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

The following examples are provided for illustrative purposes only and are not intended to limit the scope of the invention. All temperatures are in degrees Celsius unless otherwise indicated. Amberlite CG-50 is a trademark of Rohm & Haas Co., Philadelphia, Pa., U.S.A., for a weakly acidic cationic exchange resin of the carboxylic acid type. Diaion HP-20 is a trademark of Mitsubishi Chemical Industries, Japan, for a nonionic macroreticular polymer resin.

EXAMPLE 1

Fermentation of BBM-2478A and B

A well-grown slant of actinomycete strain No. J907-21 was used to inoculate a vegetative medium consisting of 3% soluble starch, 1% Bacto-liver (Difco), 0.5% fishmeal, 0.3% NaCl, 0.1% $(NH_4)_2SO_4$ and 0.6% $CaCO_3$, the pH being adjusted to 7.0 before sterilization. The vegetative medium was incubated at 28° C. for 72 hours on a rotary shaker (250 rpm) and 5 ml of the growth was transferred into a 500-ml Erlenmeyer flask containing 100 ml of a fermentation medium having the same composition as the vegetative medium. The fermentation was carried out on the rotary shaker at 28° C. for 7 to 10 days. The antibiotic activity in the fermentation broth was determined by the paper disc-agar diffusion method using *Micrococcus luteus* PCI 1001 as the test organism. Antibiotic productivity reached a maximum potency of 150 mcg/ml after 6 to 7 days' fermentation.

EXAMPLE 2

Isolation and Purification of BBM-2478A and B

Harvested broth (20 L, pH 6.8) prepared as in Example 1 was separated to mycelial cake and supernate by using a Sharpless-type centrifuge (Kokusan No. 4A). The mycelial cake was extracted three times with 5 L each of methanol. After removal of the insolubles by filtration, the methanolic extracts were combined and concentrated in vacuo to an aqueous solution. The supernate of fermentation broth was extracted with n-butanol (20 L) and the extract evaporated in vacuo to an aqueous solution. The two aqueous concentrates were combined and applied on a column of Diaion HP-20 (Mitsubishi Chem. Industries, Tokyo, $\phi 5.5 \times 60$ cm) which was developed successively with water (5 L), 50% aqueous methanol (5 L) and 80% aqueous methanol (6 L). The fractions containing BBM-2478 were monitored by paper disc assay using *B. subtilis* M45 (Rec$^-$) as the test organism. The active fractions eluted with 80% aqueous methanol were pooled, evaporated under reduced pressure and freeze-dried to give 4.5 g of yellow solid of crude BBM-2478 complex. The crude complex was applied on a column of silica gel ($\phi 3.5 \times 55$ cm) which was pre-washed with chloroform, and the activity eluted by chloroform-methanol mixture with stepwise increase of methanol concentration (5~10% v/v). The first active fractions eluted by 5% methanol were collected, concentrated in vacuo and lyophilized to afford BBM-2478B (72 mg). The second active fractions eluted by 10% methanol were similarly worked up to give semi-pure solid of BBM-2478A (2.51 g). The latter solid was further chromatographed on silica gel using a medium pressure liquid chromatogram (column: Kiriyama $\phi 11 \times 500$ mm; pump: FMI Lab pump, pressure 80~90 psi). Elution with chloroform-methanol (97:3, v/v) gave active fractions which, upon concentration in vacuo, afforded homogeneous solid of BBM-2478A (1.30 g). This solid was crystallized from methanol yielding yellowish orange rods of BBM-2478A monohydrate.

We claim:

1. The antibiotic BBM-2478A having the formula

2. The antibiotic BBM-2478B having the formula

3. A method for therapeutically treating an animal host affected by a bacterial infection which comprises administering to said host an effective antibacterial dose of BBM-2478A as defined in claim 1.

4. A method for therapeutically treating an animal host affected by a bacterial infection which comprises administering to said host an effective antibacterial dose of BBM-2478B as defined in claim 2.

5. A method for therapeutically treating a mammalian host affected by a malignant tumor selected from P388 leukemia, L1210 leukemia or B16 melanoma which comprises administering to said host an effective tumor-inhibiting dose of BBM-2478A as defined in claim 1.

6. A pharmaceutical composition comprising an effective antibacterial amount of BBM-2478A as defined in claim 1 in combination with a pharmaceutical carrier or diluent.

7. A pharmaceutical composition comprising an effective antibacterial amount of BBM-2478B as defined in claim 2 in combination with a pharmaceutical carrier or diluent.

8. A pharmaceutical composition for treatment of a mammalian host affected by a malignant tumor selected from P388 leukemia, L1210 leukemia or B16 melanoma comprising an effective tumor-inhibiting amount of BBM-2478A as defined in claim 1 in combination with a pharmaceutical carrier or diluent.

* * * * *